(12) United States Patent
Feller

(10) Patent No.: US 7,353,721 B2
(45) Date of Patent: Apr. 8, 2008

(54) FLUID SAMPLING DEVICE

(76) Inventor: Robin L. Feller, P.O. Box 926, Brownsburg, IN (US) 46112

( * ) Notice: Subject to any disclaimer, the term of this patent is extended or adjusted under 35 U.S.C. 154(b) by 240 days.

(21) Appl. No.: 10/887,117

(22) Filed: Jul. 8, 2004

(65) Prior Publication Data

US 2006/0005639 A1    Jan. 12, 2006

(51) Int. Cl.
*G01N 1/00*    (2006.01)
(52) U.S. Cl. .................................................. 73/864.51
(58) Field of Classification Search ............. 73/864.51, 73/864.52, 864.61–864.67
See application file for complete search history.

(56) References Cited

U.S. PATENT DOCUMENTS

| | | | | |
|---|---|---|---|---|
| 3,960,021 A | * | 6/1976 | Jones | 73/864.51 |
| 4,215,580 A | * | 8/1980 | Barsaloux | 73/864.66 |
| 4,754,656 A | * | 7/1988 | Charm | 73/864.63 |
| 4,949,582 A | * | 8/1990 | Vollweiler | 73/864.63 |
| 5,307,695 A | * | 5/1994 | Sawchuk | 73/864.51 |
| 5,442,970 A | * | 8/1995 | Hutchins | 73/864.63 |

* cited by examiner

*Primary Examiner*—Robert Raevis
(74) *Attorney, Agent, or Firm*—Butzel Long

(57) ABSTRACT

A modular fluid sampling device that includes an elongated handle and a sample container holder attached to one end of the elongated handle. The sample container holder is configured to receive a removable sample container therein, a bottom which is configured to allow the free floe of fluid therethrough but prevent a sample container placed within the sample container holder to pass through the bottom, and an structure that secures a sample container to the sample container holder. All the components of the sampling device are made of plastic materials that will not contribute to sample contamination and the components of the sampling device are secured together by mechanical elements in order to avoid the use of glues and adhesives. The components are sized to allow packaging and portability of the sampling device.

12 Claims, 4 Drawing Sheets

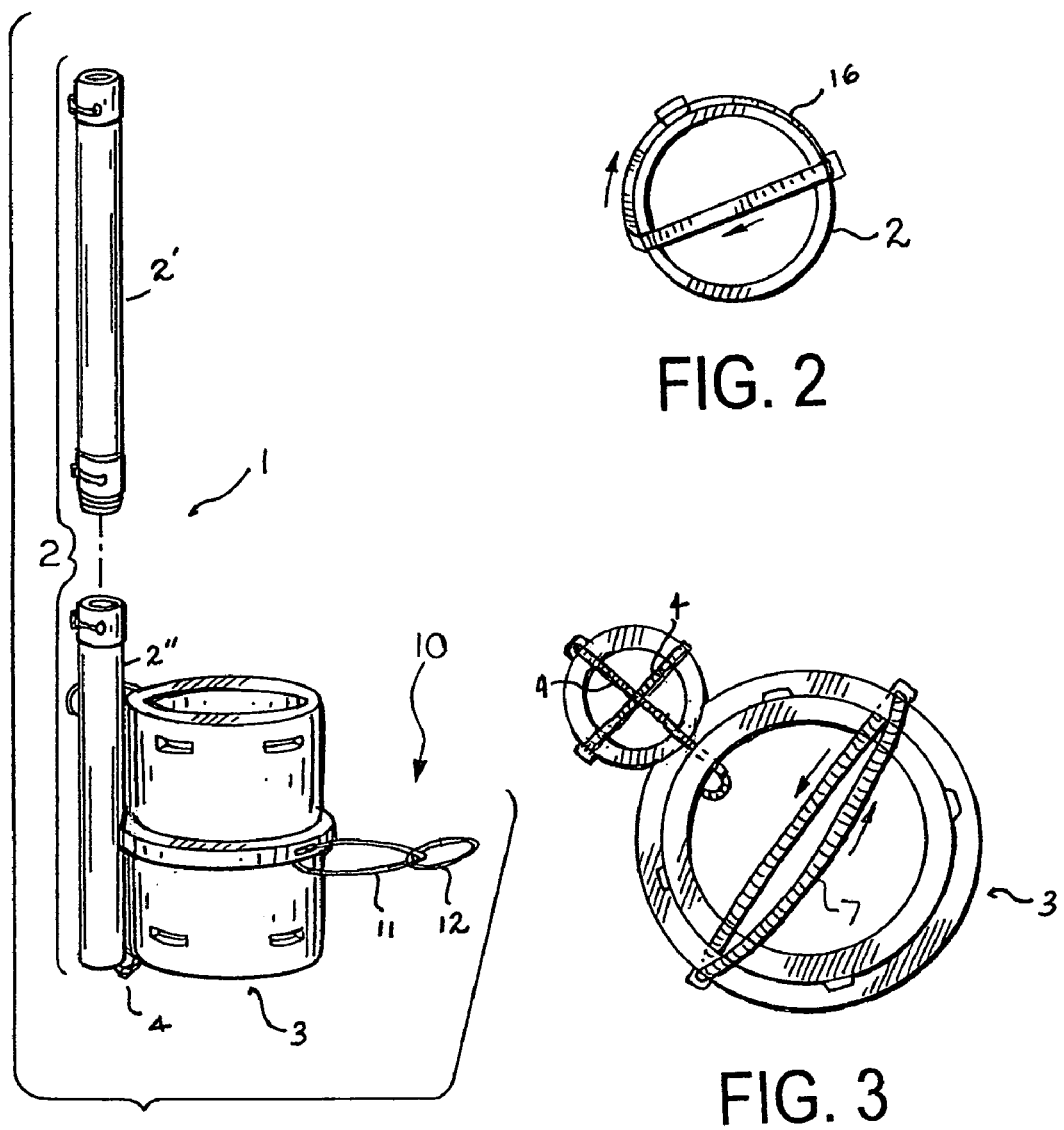

FLUID SAMPLING DEVICE

TECHNICAL FIELD

The present invention relates to devices and methods for obtaining samples from bodies of fluids for analytical purposes. Moreover, the present invention is directed to fluid sampling devices that can be at least partially disassembled for purposes of making the devices portable.

BACKGROUND ART

Recently enacted Environmental Protection Agency (EPA) regulations require communities to sample wastewater at their municipal wastewater treatment plants for low level amounts of mercury expressed in nanograms per liter (parts per trillion). Due to this relatively new sampling requirement, a need for fluid sampling methods and apparatus has been created. Fluid samples from water or wastewater sources needed to perform the EPA Test Method 1631 are typically obtained using a small pump that pumps water or wastewater through a length of plastic tubing and into a specially cleaned laboratory glass bottle. The bottled sample is thereafter transported to a laboratory that is equipped to analyze the sample for trace amounts of mercury.

The EPA sampling procedure for EPA Test Method 1631 is referred to as the "clean hands-dirty hands" technique. EPA developed this sampling procedure and the equipment/apparatus used in the procedure to eliminate the possibility of contaminating the samples with mercury from sources outside of the fluid to be tested. Both the sampling personnel and laboratory personnel take great efforts to make sure sample contamination does not occur.

The present invention provides a sampling device that meets the requirements of the EPA for sampling fluids for analytical testing procedures.

DISCLOSURE OF THE INVENTION

According to various features, characteristics and embodiments of the present invention which will become apparent as the description thereof proceeds, the present invention provides a modular fluid sampling device that includes an elongated handle and a sample container holder attached to one end of the elongated handle. The sample container holder comprises a chamber that is configured to receive a removable sample container therein, a bottom which is configured to allow the free flow of fluid therethrough but prevent a sample container placed within the sample container holder to pass through the bottom, and a means to secure a sample container to the sample container holder. The sample container holder comprises a side wall that is provided with fluid vent openings.

According to one embodiment of the present invention all the components of the fluid sampling device are made from plastic and are only mechanically coupled together. The means to mechanically couple the components together comprise at least one of ties, straps, pins, bolts, clips, rods, dowels, retainers and combinations thereof.

The means used to secure a sample container to the sample container holder comprises a tether. An alternative means to secure a sample container to the sample container holder comprises an openable closure on a top of the sample container holder which closure is configured to allow the free flow of fluid therethrough but prevent a sample container placed within the sample container holder to pass through the top. The openable closure can be removable.

The handle of the fluid sampling device comprises a plurality of handle sections that are detachable coupled to one another, including a lowermost handle section to which the sample container holder is secured. Each of the handle sections include cooperating coupling elements at opposite ends thereof which can be attached to the opposite ends of the handle sections by mechanical means.

BRIEF DESCRIPTION OF DRAWINGS

The present invention will be described with reference to the attached drawings which are given as non-limiting examples only, in which:

FIG. 1 is a side view of a sampling device according to one embodiment of the present invention.

FIG. 2 is a top cross sectional view depicting how the sections of the handle are secured together according to one embodiment of the present invention.

FIG. 3 is a top cross sectional view depicting how the sample container holder is coupled to the handle according to one embodiment of the present invention.

BEST MODE FOR CARRYING OUT THE INVENTION

Figure 4:
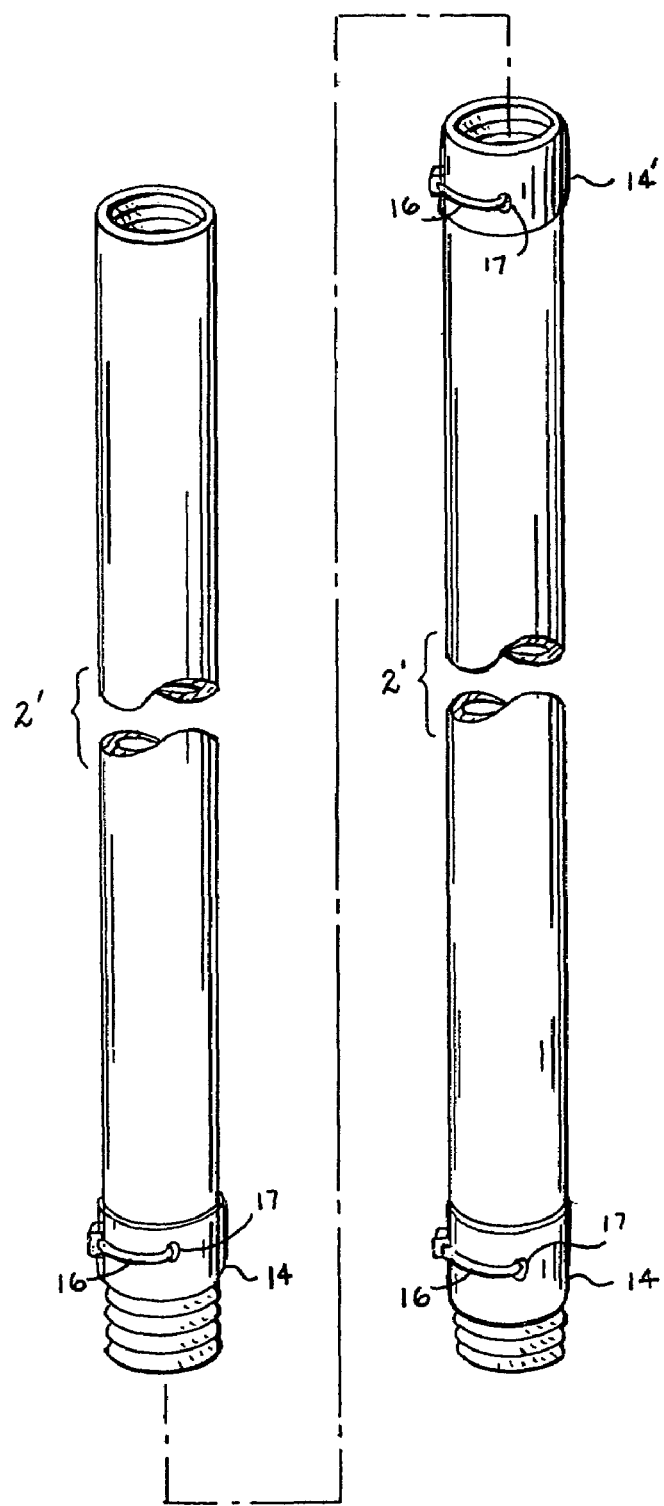
FIG. 4 is an exploded view of a multi-piece handle assembly according to one embodiment of the present invention.

The present invention is directed to methods and devices for sampling fluids from either a still or flowing source of the fluids. The methods and devices of the present invention are particularly useful to sample fluids for purposes of testing the fluids for trace amounts of elements and compounds. The methods and devices of the present invention are particularly useful for sampling water and/or wastewater for purpose of testing the samples for mercury contamination and allowing communities comply with EPA Test Method 1631.

The sampling device of the present invention and its method of use allow an individual to conduct a sampling process manually at any desired depth in a still or flowing body of fluid in a site facility such as a water filtration or treatment facility, a holding tank or pond or at a field location.

The components of the sampling device are all made of materials such as plastics which will not contribute to contamination of any fluid sample obtain using the sampling device. Moreover, plastics such as PVC upon which substances do not cling are particularly suitable because they are easy to clean and decontaminate between sampling procedures. The sampling device is made from components that can easily be assembled, disassembled and cleaned between sampling procedures. Further the components are relatively small so that the sampling device can by packed and field assembled for use. According to one embodiment, the components of the sampling device other than the handle sections can be pre-cleaned and packaged in plastic bags, including reclosable or single use plastic bags.

The components of the sampling device are designed to be coupled together using mechanical means such as straps, ties, pins, clips, etc. and cooperating coupling structures such as threaded connections, bayonet connections, snap-fit connections, etc. The use of mechanical means to couple the components of the sampling device avoids the use of chemical means such as adhesives or glues which could potentially add contaminates to samples obtained with the sampling device. It is to be understood that while avoiding the use of chemical means to attach the components of the sampling device ensures less risk of contaminates, in certain situations the use of chemical means may be acceptable depending on the nature of the sample and testing to be done. However, the use of chemical means to couple the components of the sampling device together will prevent the subsequent disassembly of the sampling device, and thus efficient cleaning and re-packaging.

According to one embodiment of the present invention the sampling device of the present invention also avoids the use of metal components in order to avoid contaminating samples with metals. It is to be understood however, that metal components could be used in some instances which the contamination of samples by metals is not a concern, for example when obtaining samples that are to be tested for organic components. However, in general the use of plastic components is suitable for most test procedures and also provides for a device that has lower weight.

The sample container holder can be sized to hold sample containers that have different volumes and different shapes. According to one embodiment of the sampling device that was developed to collect samples for the EPA Test Method 1631, the sample container holder was configured and sized to hold a standard 32 ounce narrow mouth laboratory glass bottle. Such glass sample bottles were found to become very slippery when wet so that the sample container holder of the present invention had to be designed to securely hold such bottles in turbulent water.

The sample container holder is provided with vent openings which allow surrounding fluid to freely enter and flow through the sample container holder in order to obtain a sample from the fluid flow. The vent openings can be provided in any suitable pattern and size.

Over all the sampling device of the present invention is light weight, easy to assemble, disassemble and clean, and easy to handle or use and sturdy enough to withstand swift flows inside wastewater treatment plant tanks, discharges, flowing streams and other fluid flows.

The handle of the sampling device can include any number of sections that are coupled together to result in a desired length. The individual sections of the handle can be of a convenient length that allows the disassembled sampling device to be easily packaged and transported. According to one embodiment the individual sections of the handle were five feet in length. However, shorter or longer section lengths could be used. Moreover the sections do not have to all be of the same length.

FIG. 1 is a side view of a sampling device according to one embodiment of the present invention. The sampling device generally identified by reference numeral 1 includes a handle 2 and a sample container holder 3 which is configured to be attached to an end of the handle 2. The handle 2 can be made of two or more handle sections 2' which are coupled to together as discussed below. The handle sections 2' comprises lengths of plastic, e.g. PVC, tubing that are coupled together. The sample container holder 3 comprises a cylindrical tube that is attached to one of the handle sections 2'.

In the embodiment of the invention depicted in FIG. 1, that was configured to obtain samples in standard 32 ounce narrow mouth glass laboratory bottles, the sample container holder 3 was configured from a 4 inch diameter plastic pipe internal coupler. In this embodiment the ridge of the coupler that protrudes from the middle of the coupler was notched out so as to be complementarily shaped to the lower handle section 2" which was made from a 1 inch diameter PVC pipe. This notching of the ridge of the coupler allows the lower handle section 2" to lay flat against the sample container holder 3. In the illustrated embodiment of the invention the lower handle section 2" is depicted as being relatively short as compared to the remaining handle sections 2'. In this regard, it was determined that it was not necessary to thoroughly clean and package the upper portion of the handle 2 which is remote from the sample container holder 3. However, it is desirable to thoroughly clean and package the portion of the handle 2 that is in close proximity to the sample container holder 3. Accordingly, the lower handle section(s) 2" were designed to have a length that was longer than the sample container holder 3 yet short enough to be stored after cleaning in a standard plastic bag. For such purposes, the lower handle section(s) 2" can have a length of about 8 inches or longer. As indicated, several shorter lower handle sections 2' can be combined for purposes of producing an overall handle 2 having a lower portion that can be cleaned and packaged over a desired length.

Figure 5:
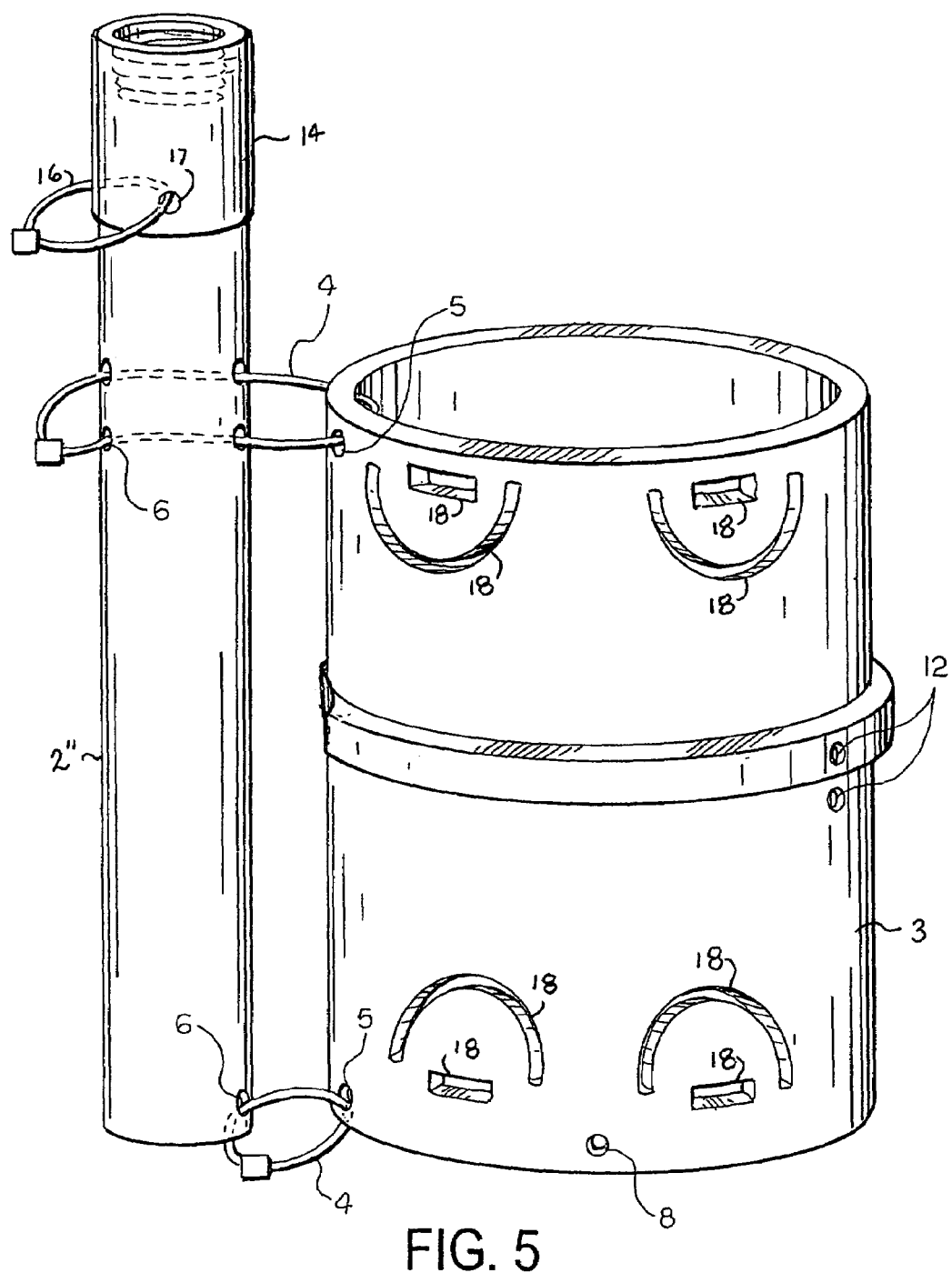
FIG. 5 is an exploded view depicting how the handle is connected to the sample container holder according to one embodiment of the present invention.
Figure 6:
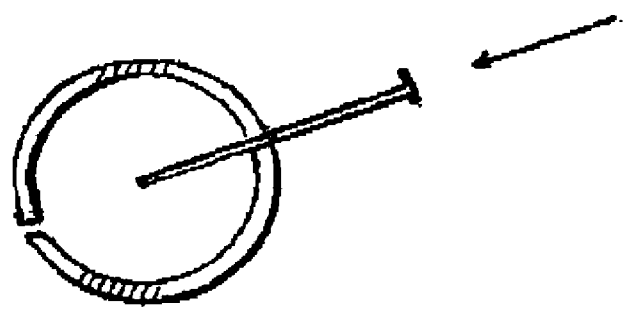
FIG. 6 is a top cross sectional view similar to FIG. 2 depicting how the sections of the handle are secured together according to another embodiment of the present invention.

The lower or lowermost handle section 2" is removable coupled to the sample container holder 3 at least near the top and bottom of the sample container holder 3 in order to provide a stable connection between the handle 2 and the sample container holder 3. In the depicted embodiment of the invention the sample container holder 3 and lower handle section 2" are secured together by self locking plastic ties 4 which are threaded through holes 5 (See FIG. 5) that are provided at the top and bottom of the sample container holder 3 and holes 6 (See FIG. 5) that are provided in the lower or lowermost handle section 2". As depicted in FIG. 5, the holes 5 in the sample container holder and the holes 6 provided in the lower or lowermost handle section 2" are aligned so that self locking plastic ties 4 can be threaded though holes 5 and 6 and tightened to secure the sample container holder 3 to the lower or lowermost handle section 2".

The bottom of the sample container holder 3 is provided with a member that prevents a sample container placed therein from passing through the bottom of the sample holder 3. In the embodiment of the invention depicted in the figures, the bottom of the sample container holder 3 is provided with a strap or web 7 that extends across the inside diameter of the sample container holder 3. According to one embodiment of the present invention the strap or web 7 is a self locking plastic tie that is threaded through holes 8 (See FIG. 5) that are provided in diametrically opposed locations in the side of the sample container holder 3 near the bottom thereof. The use of a strap or web 7 to prevent a sample container from passing through the bottom of the sample container holder 3 allows for substantial unimpeded flow of ambient fluid into the sample container holder 3. It is to be understood that the use of a self locking plastic tie for forming the strap or web 7 is only one example of a suitable means to prevent a sample container from passing through the bottom of the sample container holder 3. Alternatives include any suitable pin, bolt, clip, rod, dowel, retainer etc. that can be inserted and secured in holes 8 provided in the side of the sample container holder 3 near the bottom thereof. Moreover, two of more of such ties, straps, pins, bolts, clips, rods, dowels, retainers etc. or combinations thereof could be used and provided across the bottom of the sample container holder 3. In addition, any suitable screen, net, grate, etc. could be provided across the bottom of the sample container holder 3 and secured thereto by any suitable tie(s), pin(s), bolt(s), clip(s), rod(s), dowel(s), retainer(s), etc.

In addition to preventing the sample container from falling through the bottom of the same container holder 3, a provision is made to prevent the sample container from slipping out the top of the sample container holder 3. In this regard, consideration has to be given to the fact the when an empty sample container (containing initially only ambient air) is lowered into a body of fluid in the sample container holder 3, the sample container is buoyant and can tend to float out of the sample container holder 3. Otherwise, relative fluid flow either from ambient flow conditions or from moving the sampling device relative to a stationary point can cause a sample container to be displaced from the sample container holder 3.

In the depicted embodiment of the present invention, a tether or strap generally identified by reference numeral 10 is provided to hold a sample container in place. The tether or strap 10 comprises a first self locking plastic tie 11 that is threaded through holes 12 provided in the side of the sample container holder 3. This first self locking plastic tie 11 forms a closed loop which is long enough to extend into the interior of the sample container holder 3. A second self locking plastic tie 13 is looped through the first self locking plastic tie 11 making a second loop that is configured to be placed over the neck of a sample container (not shown) which can then rest in the sample container holder 3. The inside diameter of the sample container holder 3 is sized relative to the outside diameter of a sample container so that the sample container cannot tip over within the sample container holder 3 and spill any sample collected when the sampling device 1 is removed from a body of fluid.

Since the sample container cannot tip over, it is possible to provide the top of the sample container holder 3 with some openable or removable structure that will prevent the sample container from passing through the top of the sample container holder 3 during a sampling procedure. Such a structure can be removable ties, pins, bolts, clips, rods, dowels, retainers etc. or combinations thereof which extend the side of the sample container holder. In addition a removable screen, net, grate, etc. could be provided across the bottom of the sample container holder 3 and secured thereto by any suitable removable tie(s), pin(s), bolt(s), clip(s), rod(s), dowel(s), retainer(s), etc.

FIG. 2 is a top cross sectional view depicting how the sections 2' of the handle 2 are secured together according to one embodiment of the present invention.

The handle sections 2' include cooperating male and female threaded couplers 14 and 14' respectively which allow the handle sections 2' be connected together. In the depicted embodiment of the present invention, the male and female connectors 14 and 14' are secured on ends of the handle sections by self locking plastic ties 16 that are threaded through holes 17 that are on opposite sides of the handle sections 2' which holes 17 pass through both the handle sections 2' and the sides of the male and female connections 14 and 14' at locations that do not interfere with the threaded portions of the male and female connectors 14 and 14'. It is of course possible to couple the male and female connectors 14 and 14' to the handle sections 2' using any suitable ties, pins, bolts, clips, rods, dowels, retainers etc. It is moreover within the scope of the present invention to provide handle sections 2' with cooperating coupling structures such as threaded connections, bayonet connections, snap-fit connections, etc. molded on the ends thereof.

FIG. 3 is a top cross sectional view depicting how the sample container holder is coupled to the handle according to one embodiment of the present invention. FIG. 3 depicts one manner in which self locking plastic ties 4 and 7 could be arranged to secure the sample container holder 3 to the lowermost handle section 2" and to extend across the bottom of the sample container holder 3. As indicated above, in further embodiments of the present invention various tie(s), pin(s), bolt(s), clip(s), rod(s), dowel(s), retainer(s), etc. and/or screens, nets, grates, etc. could also be used for these functions. Moreover, it is within the scope of the present invention to provide the sample container holder 3 and lowermost handle section 2" as a unitary integral element with the bottom of the sample container holder 3 appropriately blocked to allow fluid flow there through but preventing a sample container from passing through the bottom. If is further possible to provide a removable cover over the top of the sample container holder 3 which would also be configured to allow fluid flow there through but preventing a sample container from passing through the top of the sample container holder 3. Such a cover could be completely removable or opened by a hinged, sliding or rotational movement as desired.

FIG. 4 is an exploded view of a multi-piece handle assembly according to one embodiment of the present invention. FIG. 4 depicts an upper most handle section 2" which is not required to have a male or female connector on the top thereof and an intermediate handle section 2' which is depicted as including a male connector 14 on one end and a female connector 14' on an opposite end. The male and female connectors 14 and 14' could be provided on either of the ends of the handle sections 2'. Moreover, as noted above it is within the scope of the present invention to provide handle sections 2' with cooperating coupling structures such as threaded connections, bayonet connections, snap-fit connections, etc. molded on the ends thereof or coupled thereto by any suitable ties, pins, bolts, clips, rods, dowels, retainers etc.

FIG. 5 is an exploded view depicting how the handle is connected to the sample container holder according to one embodiment of the present invention. As depicted in FIG. 5 the self locking plastic tie 4 that is used to couple the top of the sample container holder 3 to the lowermost handle section 2" is configured to be threaded through holes 6 that are provided in opposite sides of the lowermost handle section 2" while the self locking plastic tie 4 that is used to couple the bottom of the sample container holder 3 to the lowermost handle section 2" is configured to be threaded through holes 6 that are provided in opposite sides of the lowermost handle section 2" so that the bottom of the sample container holder 3 is prevented from rocking or twisting with respect to the lowermost handle section 2". As noted above, it is within the scope of the present invention to provide the sample container holder 3 and lowermost handle section 2" as a unitary integral element.

FIG. 5 illustrates venting openings 18 that are provided in the side of the sample container holder 3 so as to allow surrounding fluid to freely enter and flow through the sample container holder 3 in order to obtain a sample from the fluid flow. The vent openings 18 can be provided in any suitable pattern and size.

Although the present invention has been described with reference to particular means, materials and embodiments, from the foregoing description, one skilled in the art can easily ascertain the essential characteristics of the present invention and various changes and modifications can be made to adapt the various uses and characteristics without departing from the spirit and scope of the present invention as described above.

What is claimed is:

1. A modular fluid sampling device that comprises an elongated handle having a central axis; and
   a sample container holder having a central axis which sample container holder is attached to one end of the elongated handle so that the central axis of the sample container holder is substantially parallel to the central axis of the elongated handle,
   the sample container holder comprising chamber that is configured to receive a removable sample container therein, a bottom which is configured to allow the free flow of fluid therethrough but prevent a sample container placed within the sample container holder to pass through the bottom, a side wall that is provided with fluid vent openings, and a means to secure a sample container to the sample container holder.

2. A modular fluid sampling device according to claim 1, wherein all the components of the fluid sampling device are made from plastic and arc only mechanically coupled together.

3. A modular fluid sampling device according to claim 1, wherein components of the fluid sampling device are mechanically coupled together by at least one of ties, straps, pins, bolts, clips, rods, dowels, retainers and combinations thereof.

4. A modular fluid sampling device according to claim 1, wherein the means to secure a sample container to the sample container holder comprises a tether.

5. A modular fluid sampling device according to claim 1, wherein the means to secure a sample container to the sample container holder comprises an openable closure on a top of the sample container holder which closure is configured to allow the free flow of fluid therethrough but prevent a sample container placed within the sample container holder to pass through the top.

6. A modular fluid sampling device according to claim 5, wherein the openable closure is removable.

7. A modular fluid sampling device according to claim 1, wherein the handle comprises a plurality of handle sections that are detachable coupled to one another.

8. A modular fluid sampling device according to claim 7, wherein the plurality of handle sections include a lowermost handle section to which the sample container holder is secured.

9. A modular fluid sampling device according to claim 8, wherein the lowermost handle section and the sample container holder comprise a unitary element.

10. A modular fluid sampling device according to claim 7, wherein each of the handle sections include cooperating coupling elements at opposite ends thereof.

11. A modular fluid sampling device according to claim 10, wherein the cooperating coupling elements are attached to the opposite ends of the handle sections by mechanical means.

12. A modular fluid sampling device that comprises an elongated handle having a central axis; and
    a sample container holder having a central axis which sample container holder is attached to one end of the elongated handle so that the central axis of the sample container holder is substantially parallel to the central axis of the elongated handle,
    the sample container holder comprising chamber that is configured to receive a removable sample container therein, a bottom which is configured to allow the free flow of fluid therethrough but prevent a sample container placed within the sample container holder to pass through the bottom, and a means comprising a tether to secure a sample container to the sample container holder.

* * * * *